United States Patent [19]
Kanno

[11] Patent Number: 4,657,743
[45] Date of Patent: Apr. 14, 1987

[54] HEAT EXCHANGER-INCORPORATED HOLLOW FIBER TYPE ARTIFICAL LUNG

[75] Inventor: Michio Kanno, Miyoshi, Japan

[73] Assignee: Terumo Corporation, Tokyo, Japan

[21] Appl. No.: 753,348

[22] Filed: Jul. 8, 1985

Related U.S. Application Data

[63] Continuation of Ser. No. 440,578, Nov. 10, 1982, abandoned.

[30] Foreign Application Priority Data

Nov. 18, 1981 [JP] Japan .................. 56-183713

[51] Int. Cl.⁴ .......................................... A61M 1/03
[52] U.S. Cl. ............................... 422/46; 210/321.4; 210/450
[58] Field of Search .................. 210/450, 321.3, 321.4; 422/46, 48

[56] References Cited

U.S. PATENT DOCUMENTS

| | | | |
|---|---|---|---|
| 3,979,295 | 9/1976 | Markley | 210/493.1 X |
| 4,242,203 | 12/1980 | Amicel et al. | 210/321.1 |
| 4,283,284 | 8/1981 | Schnell | 210/450 X |
| 4,376,095 | 3/1983 | Hasegawa | 422/46 |
| 4,414,110 | 11/1983 | Geel et al. | 422/48 X |

*Primary Examiner*—Frank Spear
*Attorney, Agent, or Firm*—Frishauf, Holtz, Goodman & Woodward

[57] ABSTRACT

A heat exchanger-incorporated hollow fiber type artificial lung comprises an artificial lung part composed of a first housing, a bundle of multiple gas-exchange hollow fiber membranes enclosed with the first housing, partitions formed at the opposite ends of the bundle of hollow fiber membranes, and a blood passage and an oxygen chamber both defined by the first housing, the bundle of hollow fiber membranes, and the partitions. A heat exchanger part is composed of a second housing, a plurality of tubes enclosed with the second housing, partitions formed at the opposite ends of the tubes, and a blood passage and a heat exchange chamber both defined by the second housing, the tubes and the partitions. The artificial lung part and the heat exchanger part are connected to each other by having their respective first and second housings coaxially joined so as to give rise to a blood chamber between the opposed partitions of first and second housings. The connection between the artificial lung part and the heat exchanger part is accomplished by forming connecting ends one each at the opposed sides of the two housings, joining the connecting ends across an annular spacer by virtue of a connecting ring fitted across the outer surfaces of the connecting ends and, through at least two holes bored in the connecting ring so as to communicate with the vacant part defined by the connecting ring, the opposed partitions, and the annular ring. An adhesive agent is then injected through the holes so as to fill up the interior of the vacant part.

9 Claims, 3 Drawing Figures

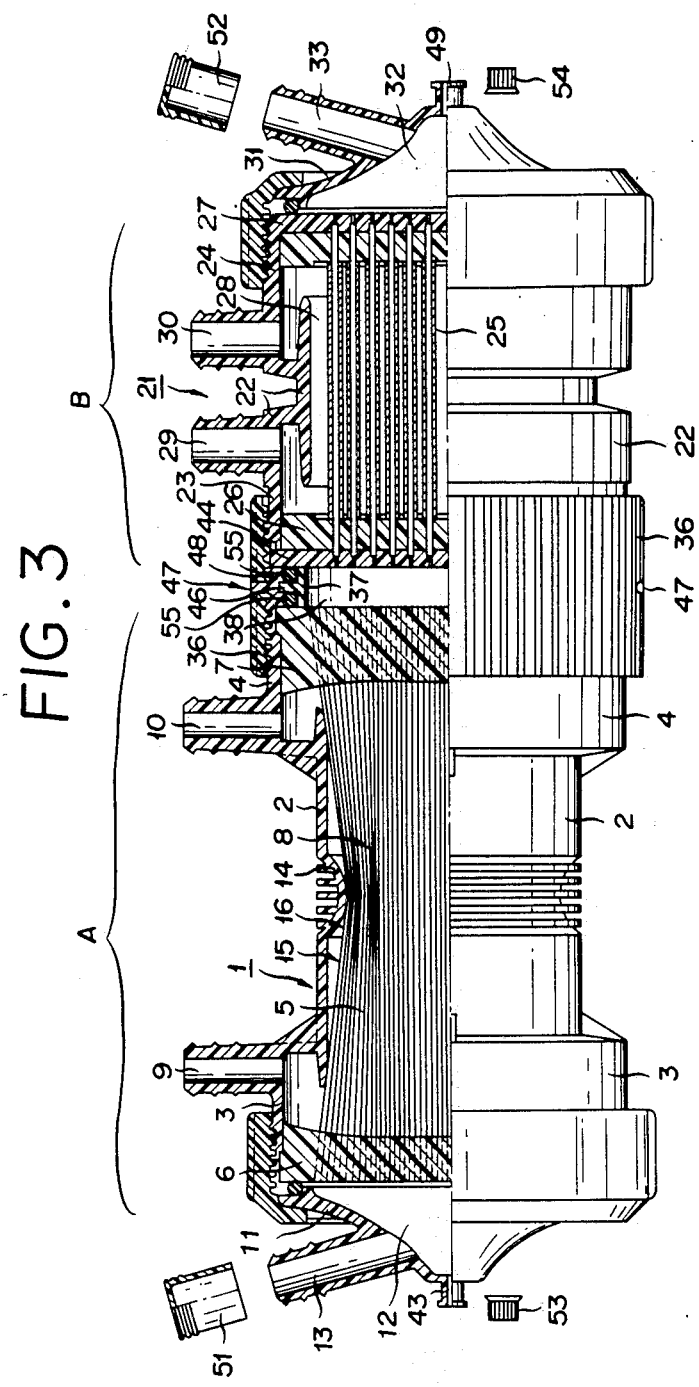

HEAT EXCHANGER-INCORPORATED HOLLOW FIBER TYPE ARTIFICAL LUNG

This application is a continuation of application Ser. No. 440,578, filed Nov. 10, 1982, now abandoned.

BACKGROUND OF THE INVENTION

1. Field of the Invention

This invention relates to an improved heat exchanger-incorporated hollow fiber type artificial lung 2. Description of the Prior Art Generally, when blood is drawn out of a patient's body and oxygenated externally as during a cardiac operation, an artificial lung is used in the extracorporeal circut. When the cardiac operation necessitates use of slighly or medially low temperatures or extremely low temperatures, the blood must be cooled to the order of 35° to 20° C. at the outset of the circulation of blood through the extracorporeal circuit. Conversely when the extracorporeal circulation is to be terminated, the blood must be heated to a temperature substantially equal to the patient's body temperature. For the purpose of this regulation of blood temperature, the extracorporeal circuit is provided with a heat exchanger. This heat exchanger may be utilized for the purpose of maintaining the warmth of blood when the blood is desired to be circulated at the normal body temperature.

Conventionally in the extracorporeal circuit, the artificial lung and the heat exchanger have been incorporated independently of each other and interconnected with a connection tube. As a consequence of this setup, the assemblage of the circuit has proved complicated and the connection between the artificial lung and the heat exchanger has sometimes been made incorrectly, though not frequently. Moreover, since the connection tube is inevitably provided with two independent blood ports (one for the heat exchanger and the other for the artificial lung), it has called for a large volume of priming. Further, the operation of priming itself has been quite difficult because the removal of bubbles from the blood during the course of priming must be performed separately for the artificial lung and the heat exchanger.

As a partial solution of this problem, a superposed membrane type artificial lung incorporating a heat exchanger has been disclosed in Japanese Patent Publication (Kokoku) No. 2982/1980. Since the artificial lung part and the heat exchanger part are both of a superposed membrane type, the artificial lung is difficult to manufacture. Moreover, the artificial lung of such a membrane type admits a heavy personal error and has a possibility of entailing dispersion of quality among artificial lungs manufactured at one and the same factory.

To solve the problem, a heat exchanger-incorporated hollow fiber type artificial lung has been proposed. The lung includes a hollow fiber type artificial lung part having a plurality of bundles of gas-exchange hollow fiber membranes contained in a first tubular housing, and a shell-and-tube type heat exchanger part having a plurality of tubes contained in a second tubular housing, with the aforementioned artificial lung part and the aforementioned heat exchanger part coaxially connected to each other through the union of the first and second tubular housings (Japanese Patent Application No. 115,868/1980). In this artificial lung, the first and second housing have connecting ends of an identical diameter. These connecting ends have screw threads cut in manually opposite directions. The first and second housings are connected to each other through the medium of an O-ring by virtue of a connecting screw ring fitted across the outer sides of the aforementioned connecting ends.

The artificial lung adopting such mode of connection as described above is effective for a short period of time. When this artificial lung as a product is required to guarantee good performance for a long time, it may possibly pose some problems. If the screw threads in the connecting ends should come loose, since one of them spirals opposite the other, the user could not easily retighten them. When he dares to retighten such loose screw threads, thre is a possibility that he will unwittingly cause them to separate from each other entirely. In the hope of precluding such problem the feasibility of a method of fusing the reverse screw ring fast in position has been studied, only to find that the potting member of the artificial lung would collapse on prolonged exposure to compression, and the O-ring made of rubber would avoid following the collapse and induce leakage. When the O-ring separates from the groove formed exclusively for its insertion, it will induce leakage afterward.

An object of this invention is to provide a heat exchanger-incorporated hollow fiber type artificial lung provided with a highly relieable, safe connection structure.

SUMMARY OF THE INVENTION

The object described above is attained by a heat exchanger-incorporated hollow fiber type artificial lung comprising a hollow fiber type artificial lung part composed of a first housing, a hollow fiber bundle of a plurality of gas-exchange hollow fiber membranes mutually separated and parallelly disposed within the first housing in the longitudinal direction of the housing, a first and a second partition water-tightly supporting the hollow fiber membranes at the opposite ends thereof in a state not blocking the openings of the membranes and further defining an oxygen chamber in conjunction with the inner wall of the first housing and the outer surfaces of the hollow fiber membranes, an oxygen inlet and an oxygen outlet communicating with the oxygen chamber, and a blood passage communicating with the cavities in the hollow fiber membranes at the outside thereof on the first partition side and a shell-and-tube type heat exchanger part composed of a second housing, a plurality of tubes mutually separated and parallelly disposed inside the second housing in the longitudinal direction, a third and fourth partition water-tightly supporting the tubes at the opposite ends thereof in a state not blocking the openings of the tubes and further defining a heat-exchange medium chamber in conjunction with the inner wall of the second housing and the outer surfaces of the tubes, a heat-exchange medium inlet and a heat-exchange medium outlet communicating with the heat-exchange medium chamber, and a blood passage communicating with the cavities inside the tubes at the outside thereof on the fourth partition side, wherein the artificial lung part and heat exchanger part are coaxially connected to each other in the first and second housing so as to give rise to a blood chamber between the second partition and third partition, wherein the heat exchanger-incorporated hollow fiber type artificial lung is arranged so that the first and second housings have connecting ends formed one each therein so as to be connected to each other through the medium of an annular spacer by virtue of a connecting ring fitted across the outsides of the connecting ends and, through at least two injection holes bored in the connecting ring so as to communicate with a vacant part defined by the connecting ring, the third and fourth partitions, and the annular spacer, and adhesive agent is injected to fill up the vacant part.

In a preferred embodiment of this invention, the first and second housings possess their own connecting ends of an identical diameter and these connecting ends have screw threads cut in oppositely spiralling directions and are connected with a connecting screw ring. The annular spacer adapted to form the blood chamber between the second and third partitions has a protuberance formed on the periphery thereof. A gap formed between this protuberance and the second partition and a gap formed between the protuberance and the third partition each have an O-ring inserted therein.

The hollow fiber membranes are formed of polyolefin, for example. Generally, this polyolefin hollow fiber membrane contains pores of an average diameter of about 200 to about 2,000 Å at a porosity of about 20 to about 80%. The average diameter of the pores in the hollow fiber membrane is determined as follows. First, the inner and outer surfaces of a given sample membrane are observed in conjunction with standard particles (such as, for example, "Uniform Latex Particles" made by the Dow Chemical Company) under a scanning electron microscope (made by Nihon Denshi Kabushiki Kaisha) at about 10,000 magnifications to compare the fine pores in the sample membrane with the standard particles and determine the diameters of such pores based on the size of the standard particles. Then, the diameters of the pores having a substantially circular shape are averaged and the value thus found is noted as an average pore diameter. When the pores have an elliptic shape, their major diameters and minor diameters are measured and the areas of these ellipses are calculated by the formula, $S=\pi ab/4$ (wherein, S denotes the area, a the major diameter, and b the minor diameter). The diameters of the pores are then calculated by assuming the found areas as areas of circles. They are averaged. The value so found is noted as the average pore diameter. In other words, the average diameter of such elliptic pores represents a geometric mean of major and minor diameters.

Further in the preferred embodiment of this invention, the first housing is provided on the inner wall thereof with a constricting part adapted to squeeze the bundles of hollow fiber membranes at a point halfway along the entire length of the bundles.

BRIEF DESCRIPTION OF THE DRAWINGS

FIG. 3 is a partially sectioned side view of another embodiment of the present invention.

PREFERRED EMBODIMENT OF THE INVENTION

Figure 1:
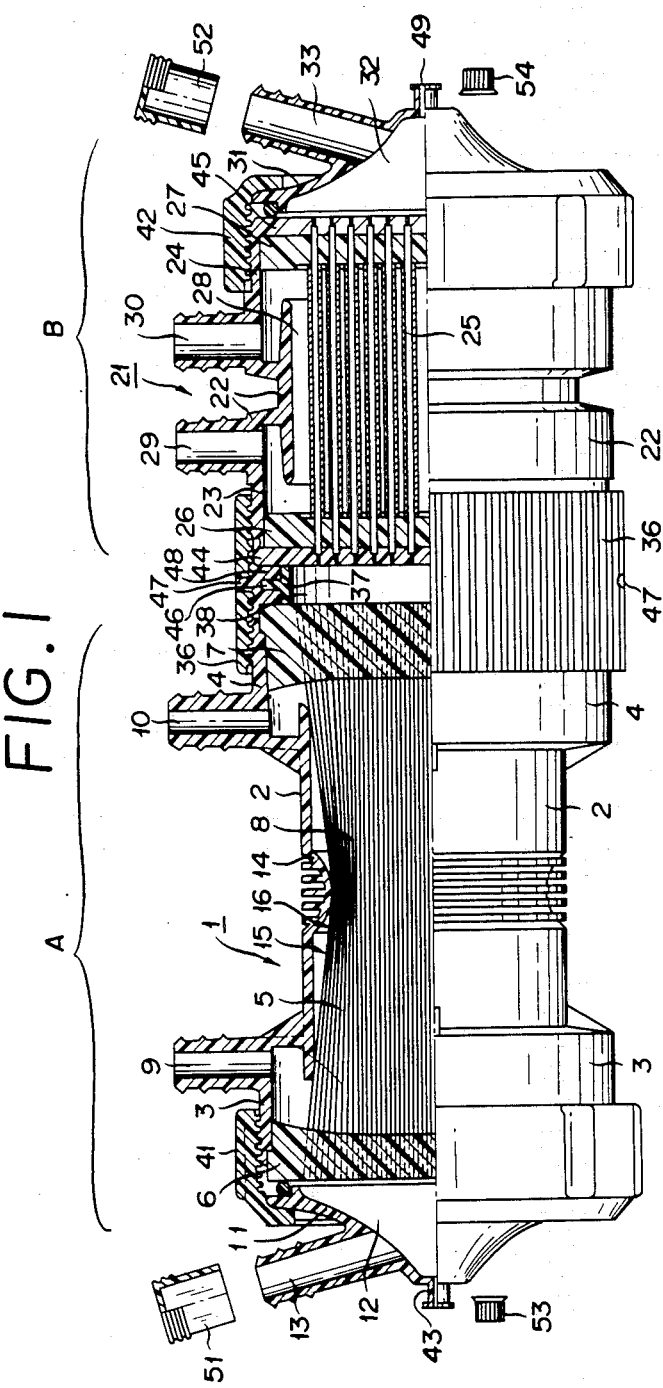
FIG. 1 is a partially sectioned side view of one preferred embodiment of the heat exchanger-incorporated hollow fiber type artificial lung according to this invention.

As illustrated in FIG. 1, the heat exchanger-incorporated hollow fiber type artificial lung of this invention has a hollow fiber type artificial lung part A and a heat exchanger part B integrally connected to each other. The artificial lung part A is provided with a first housing 1. The first housing 1 is provided, at the opposite ends of a cylindrical main body 2 which forms part of the housing 1, with annular male screw thread fitting covers 3, 4. Inside the first housing 1, a multiplicity, specifically on the order to 10,000 to 60,000 in total, of gas-exchange hollow fiber membranes 5 are parallelly arranged, while mutually separated, longitudinally to full capacity. Inside the annular fitting covers 3, 4, the opposite ends of the gas-exchange hollow fiber membranes 5 are water-tightly supported in position by a first partition 6 and a second partition 7 in such a manner that the openings of the individual membranes may not be blocked. The aforementioned partitions 6, 7 define and enclose an oxygen chamber 8 in conjunction with the outer surfaces of the hollow fiber membranes 5 and the inner wall surfaces of the aforementioned first housing 1. They further separae the oxygen chamber 8 from cavities formed inside the aforementioned gas-exchange hollow fiber membrane 5 for passage of blood (not shown).

The annular fitting cover 3 is provided with an inlet 9 for supply of oxygen and the other annular fitting cover 4 is provided with an outlet 10 for discharge of oxygen.

The outer surface of the first partition 6 is covered with a blood port 11. The inner surface of the blood port 11 and the surface of the first partition 6 define a blood inflow chamber 12. Further, in the blood port 11 is formed an inlet 13 for blood. The blood port 11 is fastened to the fitting cover 3 with a screw ring 41. The blood port 11 is also provided with an air vent 43.

The cylindrical main body 2 of the first housing 1 is preferably provided on the inner wall surface thereof with a constricting member 14 protuberating at a position halfway along the axial length thereof. To be specific, the constricting member 14 is integrally formed with the cylindrical main body 2 on the inner wall side of the main body so as to squeeze the overall periphery of the hollow fiber bundle 15 comprising the multiplicity of hollow fiber membranes 5 inserted axially in the interior of the cylindrical main body 2. Thus, the hollow fiber bundle 15 is constricted at a point falling halfway along the axial length thereof as illustrated in FIG. 1 to form a squeezed portion 16. The packing ratio of the hollow fiber membranes 5 continuously varies in the axial direction thereof, reaching the maximum at the center. For a reason to be described, the values of packing ratio at varying points are desired to be as follows. First, the packing ratio in the squeezed portion 16 at the center is about 60 to 80%, that inside the cylindrical main body 2 about 30 to 60%, that at the opposite ends of the hollow fiber bundle 15, namely on the outside of the partitions 6, 7 about 20 to 40%.

The hollow fiber membranes 5 are made of porous polyolefin resin such as, for example, polypropylene resin or polyethylene resin. Among other polyolefin resins, the polypropylene resin proves particularly desirable. These hollow fiber membranes 5 can be obtained in a form containing numerous pores interconnecting the inside and the outside of the partition. The inside diameter is about 100 to 1,000 μm, the wall thickness is about 10 to 50 μm, the average pore diameter is about 200 to 2,000 Å, and the porosity is about 20 to 80%. In the hollow fiber membranes made of such a polyolefin resin, the resistance the membranes offer to the movement of a gas therein is small and the capacity of the membranes for gas exchange is notably high because the gas moves therein in a voluminal flow. Optionally, the hollow fiber membranes may be made of silicone.

The hollow fiber membrane 5 made of porous polypropylene or polyethylene are not directly used in their unmodified form in the artificial lung but preferably have their surfaces, which are destined to contact blood, coated in advance with an antithrombotic material. For example, the surfaces may be treated with such a material as polyalkyl sulfone, ethyl cellulose or polydimethyl siloxane which excels in gas permeability, so as to be coated with a film of this material in a thickness of about 1 to 20 $\mu$m. In this case, possible dispersion of water vapor from the blood under treatment may be precluded by allowing the produced film of this material to cover the pores in the membranes to such an extent that no adverse effect will be exerted on the previousness of the hollow fiber membranes 5 to gases. Generally, during the operation of the artificial lung, the pressure on the blood side is higher than that on the oxygen side. There are times when this relationship may be reversed for some cause or other. If this reversal occurs, there may ensue the possibility of microbubbles flowing into the blood. When the hollow fiber membranes have their pores coated with an antithrombotic material as described above, this possibility is completely avoided. Of course, this coating is also useful for preventing the blood from coagulation (occurrence of microclots).

Now, the formation of the aforementioned first and second partitions 6, 7 will be described. As described above, the first and second partitions 6, 7 fulfil an important function of isolating the interiors of the hollow fiber membranes 5 from the ambience. Generally, the partitions 6, 7 are produced by centrifugally casting a high molecular potting agent of high polarity such as, for example, polyurethane, silicone or epoxy resin, in the inner wall surfaces at the opposite ends of the first housing 1 and allowing the cast potting agent to cure in place. To be more specific, a multiplicity of hollow fiber membranes 5 of a length greater than the length of the first housing 1 are prepared and, with their opposed open ends filled up with a highly viscous resin, disposed parallelly within the cylinderical main body 2 of the first housing 1. Then, the opposite ends of the hollow fiber membranes 5 are completely concealed with mold covers of a diameter greater than the diameter of the fitting covers 3, 4. The high molecular potting agent is cast through the opposite ends of the first housing 1 at the same time that the first housing 1 is rotated about its own axis. After the resin has been cast and cured fully, the aforementioned mold covers are removed and the outer surface portions of the cured resin are cut off with a sharp cutter to expose the opposite open ends of the hollow fiber membranes 5 to view. Consequently, there have been formed the first and second partitions 6, 7.

In the embodiment described above, since the hollow fiber bundle 15 is constricted at the central portion by the constricting member 14 and expanded toward the opposite ends thereof, the packing ratio of hollow fiber membrances 5 is increased in the squeezed portion 16 and, at the same time, the individual hollow fiber membranes 5 are uniformly dispersed inside the cylindrical main body 2. Consequently, the oxygen gas is allowed to form a uniformly dispersed, stable current as compared with the hollow fiber bundle destitute of the squeezed portion 16. This means that the efficiency of exchange of oxygen for carbon dioxide gas is improved.

Further, since the internal cross section of the first housing 1 is suddenly changed in the squeezed portion 16 at the center, the flow rate of the oxygen gas in this portion is suddenly changed. Thus, the constriction of the hollow fiber bundle 15 is effective in increasing the flow rate of the oxygen gas and heightening the speed of movement of the carbon dioxide gas as well.

The packing ratio of hollow fiber membranes 5 in the squeezed portion 16 is desired to be fixed in the range of about 60 to 80% for the following reason. If the packing ratio is less than about 60%, part of the hollow fiber membranes 5 escape being squeezed by the constricting member 14. Consequently, the performance of the hollow fiber membranes is impaired because they are unevenly distributed to an extent of inducing the phenomenon of channeling. Further, there is posed a problem that the hollow fiber bundle 15 cannot be accurately disposed at the center of the cylindrical main body with ease. If the packing ratio is more than about 80%, those of the hollow fiber membranes 5 held in direct contact with the constricting member 14 are depressed so powerfully as to be crushed. Consequently, blood fails to flow through the crushed hollow fiber membranes, lowering the overall efficiency of the hollow fiber fundle and inducing the phenomenon of blood stagnation. Moreover, during the assemblage of the artificial lung part, the constricting member 15 permits no easy passage of the hollow fiber bundle 15, making the work very difficult.

The packing ratio of hollow fiber membranes inside the cylindrical main body 2 has been fixed in the range of about 30 to 60% for the following reason. If the packing ratio is less than about 30%, the hollow fiber membranes 5 are deviated to one side in the interior of the cylindrical main body 2 and, consequently, the efficiency of exchange of oxygen gas for carbon dioxide gas is degraded. The work involved also becomes difficult. If the packing ratio is more than about 60%, mutual contact of hollow fiber membranes 5 occurs and exerts an adverse effect upon the performance of the hollow fiber bundle.

The packing ratio of hollow fiber membranes outside the first and second partitions 6, 7 has been fixed in the range of about 20 to 40% for the following reason. If this packing ratio is less than about 20%, the uniformity of the distribution of hollow fiber membranes 5 at the opposite open ends tends to be degraded by reason of workmanship. Consequently, such problems as ununiform blood flow distribution and blood clotting ensue. If the packing ratio is more than about 40%, mutual contact of hollow fiber membranes 5 occurs and prevents the potting agent, the materials for the first and second partitions 6, 7, from being evenly cast throughout the entire inner wall surfaces at the opposite ends of the cylindrical main body. Consequently, the produced first and second partions 6, 7 will suffer from leakage.

In the embodiment so far described, only the constricting member 14 is partially projected from the inner wall surface of the first housing 1. This is not necessarily the sole means of imparting required constriction upon the hollow fiber bundle. It may be otherwise obtained by separately forming a ring-shaped constricting member and fitting it in position on the interior of the cylindrical main body. It may be obtained by forming an annular recess at the center of the cylindrical main body. Optionally, the cylindrical main body may be gradually converged inwardly from the opposite ends thereof so that the inside diameter thereof reaches its minimum at the center and its maximum at the opposite ends.

The heat exchanger part B has a second housing 21 which comprises a cylindrical main body 22 similar in shape to the first housing 1 of the artificial lung part A, fitting covers 23, 24 provided respectively with heat-exchange medium inlet 29 and outlet 30 and each incorporating a male screw thread, and a blood port 31 containing a blood outlet 33. Inside the second housing 21, a multiplicity of tubes 25 are mutually separated and parallelly disposed in the longitudinal direction of the second housing 21, with their opposite ends supported in position inside the fitting covers 23, 24 with third and fourth partitions 26, 27 formed similarly with a potting material. The third and fourth partitions 26, 27 define a heat exchange medium chamber 28 in conjunction with the outer surfaces of the tubes and the inner wall surfaces of the second housing 21. Optionally, to the outer sides of the third and fourth partitions 26, 27 are respectively attached a first end face member 44 and a second end face member 45. The tubes 25 are slender tubes measuring 1 to 3 mm in inside diameter, 0.05 to 0.2 mm in wall thickness, and 50 to 300 mm in length and made of a thermally resistant, inexpensive material having high thermal conductivity and high rigidity enough to escape being bent even when molded in a small wall thickness. Preferably, the mateial is a metal such as stainless steel.

Figure 2:
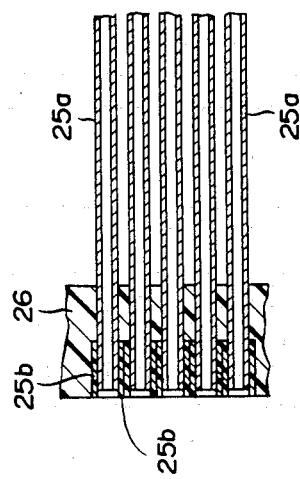
FIG. 2 is an enlarged cross section of an end portion of the heat exchanger part illustrated in FIG. 1.

The tubes 25 may be composed of such slender tubes 25a as described above and plastic tubes 25b as illustrated in FIG. 2. In this case, the plastic tubes 25b of rigid resin such as silicone or polyurethane with Shore A hardness of 95 to 98 measuring slightly smaller in inside diameter than the outside diameter of the slender tubes 25a, about 1 mm in wall thickness, and 20 to 50 mm in length are slipped over the opposite end portions of the slender tubes 25a of the aforementioned dimensions to a length of about 5 mm each. These plastic tubes 25b are preferably made of a material having chemical and physical properties approximating the corresponding properties of the pressureproof partitions 26, 27 supporting in position the tubes 25. When the pressureproof partitions 26, 27 are made of polyurethane, for example, the plastic tubes 25b are desired to be made of polyurethane. When the material for the partitions 26, 27 and that for the plastic tubes 25b have no affinity for each other as when the former is polyurethane and the latter is polyethylene, for example, the surface of the plastic tubes 25b must be treated so as to acquire affinity for the material of the slender tubes 25a. To be specific, the outer surface of the plastic tubes 25b must be oxidized with a suitable chemical or flame or subjected to a physical treatment by corona discharge or plasma discharge, for example.

The shell-and-tube type heat exchanger B described above is produced as follows. First, the tubes 25 having the plastic tubes 25b slipped over the opposite end portions of the slender tubes 25a are prepared. Preferably, the openings at the opposite ends of the slender tubes 25a are chamfered in advance. Then, 10 to 100 tubes 25 of an identical size are bundled as one unit, with their opposed ends aligned correctly. They are tied up by fastening elastic tubes such as, for example, rubber bands round the opposite end portions of the bundled tubes. The space separating the adjacent tubes 25 can be freely changed by suitably changing the wall thickness of the plastic tubes 25b. Then, the openings at the opposite ends of the tubes are filled up. This work of filling up the openings can be performed at any desired time before the insertion of the tubes into the mold caps which is to be carried out as described fully afterward. This filling work is not required when the plastic tubes 25b used on one end of the slender tubes 25a have been sealed from the beginning. Thereafter the bundled tubes 25 are inserted into the second housing 21. In the meantime, mold caps each having a cylindrical member of a smaller diameter fitted to the leading end of a cylindrical member of a larger diameter are prepared. The mold caps are desired to be made of such material as may be molded in a given shape and may then be easily cut with a cutter. The inside diameter of the small-diameter cylindrical member of the mold cap is equal to the overall outer diameter of the bundled tubes 25 and the inside diameter of the large-diameter cylindrical member of the mold cap is nearly equal to the inside diameter of the fitting covers 23, 24 of the second housing 21. The small-diameter cylindrical members of the mold caps are inserted so as to hold the bundled tubes securely in position and the leading ends of the large-diameter cylindrical members of the mold caps are wrapped round the end portions of the fitting covers 23, 24.

When the rigid resin is cast into the interior of the outer cylinder by the centrifugal casting method, prevention of possible leakage of the rigid resin is desired to be effected by preparing compression caps having an inside contour conforming with the outside contour of the mold caps and fitting them on the mold caps already covering the opposite ends of the outer cylinder so as to exert a compressive force upon the opposite ends. Thereafter, the rigid resin such as silicone or polyurethane is cast mold through the opposite ends of the outer cylinder into the interior of the cylinder with the second housing 21 rotated about its axis for 15 to 20 minutes according to the centrifugal casting method. The cast masses of the rigid resin, on being cured, form the third and fourth pressureproof partitions 26, 27 which support the opposite ends of the tubes fast in position at the opposite openings of the outer cylinder. Then, the compression caps are removed from the opposite ends of the outer cylinder and the pressureproof partitions and the molds now supporting the tubes fast in position are cut perpendicularly to the axial direction of the outer cylinder to open the opposite ends of the tubes.

When the slender tubes of the tubes which are supported fast in position by the pressureproof partitions are made of metal, only the plastic tubes have to be cut. The slender metal tubes, therefore, remain uncut and have no possibility of producing any burr.

Subsequently, the blood port 31 is fastened with the screw ring 42 to the fitting cover 23 at one end of the second housing 21.

When the internal surfaces of the mold caps are coated in advance with a substance incapable of adhering to the rigid resin, the mold caps can be easily separated from the pressure-proof partitions 26, 27, making it no longer necessary to cut the partitions 26, 27 as covered with the mold caps. When the rigid resin is polyurethane, for example, the internal surfaces of the mold caps may be coated with fluorine type resin to ensure this easy separation of the mold caps.

In the artificial lung part A and the heat exchanger part B constructed as described above, their opposed fitting covers 4, 23 have screw threads cut thereon in mutually opposite spiralling directions as illustrated in FIG. 1. Through the medium of an annular ring 37 provided on the periphery thereof with a protuberance 46, the fitting covers 4, 23 are connected to each other with the connecting screw ring 36 fitted round their outer faces so as to define the blood chamber 38 in conjunction with the second partition and the third partition 26. Through at least two injection holes 47 bored in the scrw ring 36 so as to communicate with the vacant portion defined by the connecting screw ring 36, the third and fourth partitions 7, 26, and the annular spacer 37, an adhesive agent 48 is injected to fill up the aforementioned vacant portion. The adhesive agent 48 thus filling the vacant portion fastens the first and second housings 1, 21 and the connecting screw ring 36.

The protuberance 46 which is formed on the periphery of the annular spacer 37 may be in the form of a continuous raised strip encircling the entire periphery of the annular spacer 37. Optionally, the raised strip may be in a discontinuous form. Since the protuberance 46 is intended to enable the annular spacer 37 to be positioned coaxially with the housings 1, 21, it may be composed of three substantially equally spaced raised points. It may be omitted when the annular ring 37 has a large wall thickness. Even when this protuberance is omitted, there must be left a gap between the annular ring 37 and the connecting screw ring 36 to permit insertion of a layer of the adhesive agent. In the diagram of FIG. 1, holes 43 and 49 are used as air vent or reserved for some other purposes. These holes and the holes bored in the blood inlet 13 and the blood outlet 33 have their respective caps 51, 52, 53 and 54 attached thereto.

The adhesive agent to be used in the present invention must be in a liquid or some other similar state so as to exhibit ample flowability when it is injected through the holes 47 into the vacant portion. Thus, it is desired to be made of rigid resin which exhibits high adhesiveness at least to the fitting covers 4, 23 and the connecting screw ring 36 and further to the second partition 7, the third partition 26 (or the first end face member 44), and the annular spacer 37. As the adhesive agent, a potting agent of high polarity such as, for example, polyurethane, silicone or epoxy resin which is similar to the potting agent generally used to make the partitions 7, 26 is available. Particularly, polyurethane gives desirable results.

Among the different types of polyurethane adhesive agents, the prepolymer adhesive agent, the polyisocyanate adhesive agent and the isocyante-modified polymer are advantageously used. Generally, the prepolymer adhesive agent is a preferred choice. A typical prepolymer adhesive agent is produced by mixing a prepolymer formed of 4,4'-diphenyl methane diisocynate and a bifunctional caster oil derivative (such as, for example, polypropylene glycol ester of ricinoleic acid, having a molecular weight of 540) (with a NCO/OH ratio in the range 1:1 to 1:1.5) with a curing agent formed of a mixture of a bifunctional castor oil derivative, a polyfunctional polypropylene glycol (having a molecular weight of 2,000 to 3,000, and an amino alcohol (50–70:15–25:15–25 by weight ratio) in a weight ratio of 65:35 to 59:41, for example, so as to equalize substantially the numbers of functional groups involved. This prepolymer adhesive agent is capable of cold curing, possesses moderate elasticity, and excels in adhesiveness.

FIG. 3 represents another preferred embodiment of this invention, wherein O-rings, specifically two O-rings are placed to encircle the periphery of the annular spacer 37 as opposed to each other across the protuberance 46 and the vacant portion defined by the second partition 7, the third partition 26, the connecting screw ring 36, and the annular spacer 37 is filled with the adhesive agent 48. The O-rings and the confined adhesive agent cooperate to enhance the tightness of the closure of the blood chamber 38. The same numerical symbols used in this diagram as those of FIG. 1 denote like parts.

The embodiments of the invention described so far represent cases wherein the connecting screw ring 36 is adopted as means for connection between the first housing 1 and the second housing 21. When the adhesive agent to be used possesses ample adhesive strength, the connection of the two housings can be accomplished by using only the adhesive agent. Then, it is no longer necessary to form screw threads on the connecting ring and the fitting covers 4, 23. In this case, the parts being fastened with the adhesive agent must be kept immobilized until the adhesive agent placed to fill the vacant portion is completely cured. The connection can easily be attained by provisionally fastening these parts with adhesive tape wrapped round joints of adjacent parts, then filling the vacant portion with the adhesive agent, and peeling the adhesive tape off the joints after the adhesive agent has been completely cured. The provisional fastening of the parts may be effected by using molds of silicone rubber instead of the adhesive tape.

Generally, the fitting cover 4 which constitutes the connecting end of the first housing 1 and the fitting cover 23 which constitutes the connecting end of the second housing 21 are desired to have an identical diameter. Of course, they can have two different diameters as occasion demands. In this case, the corresponding halves of the connecting ring 36 are required to have inside diameters matched to the different diameters of the fitting covers 4, 23.

The heat exchanger-incorporated hollow fiber type artificial lung constructed as described above is inserted in the external path for blood circulation and is operated to bring about the same effect as the conventional heat exchanger and the aritifical lung which are inserted separately of each other. To be specific, the blood forwarded by a pump (not shown) is introduced through the blood inlet 13, and passed through the interiors of the hollow fiber membranes 5 via the blood inlet chamber 12. During the passage through the interiors of the hollow fiber membranes, the blood is divested of carbon dioxide gas and oxygenated with the oxygen gas introduced via the gas inlet 9 into the oxygen chamber 16 and brought to the blood chamber 38. The oxygen gas in the oxygen chamber 16 is discharged in conjunction with the released carbon dioxide gas via the outlet 10.

On reaching the blood chamber 38, the blood is forwarded through the tubes 25. During the passage through these tubes, the blood is heated or cooled with the heat exchange medium such as hot water or cold water introduced via the medium inlet 29 into the medium chamber 28. After the exchange of heat, the blood is brought to the blood outlet chamber 32 and discharged via the blood outlet 33 to be subsequently returned to the patient's body through the blood circulation path. The spent medium in the medium chamber 28 is released via the medium outlet 30.

The flow of the blood may be reversed when desired. In this case, the blood which is heated or cooled in the heat exchanger part B and then oxygenated and divested of carbon dioxide gas in the artificial lung part A is returned to the patient's body.

As described above, the present invention concerns incorporation of a heat exchanger in a hollow fiber type artificial lung. Since extra tubes otherwise required in the connection of the two parts are not used, it permits a decrease in the volume of priming. Further, the deaeration of blood at the time of priming has only to be performed just once and need not be effected independently and sequentially in the artificial lung part and the heat exchanger part. This means that the time required for the assemblage of the blood circulation path and the time spent for the deaeration of blood can be cut notably. The possibility of incorrect connection between the artificial lung and the heat exchanger is completely eliminated.

Since the artificial lung part and the heat exchanger part are joined with an adhesive agent which is placed to fill the vacant portion formed by the second and third partitions, the connecting ring, and the annular spacer, possible leakage of blood through the lines or faces of junction can be prevented completely. Since the insertion of an O-ring can be omitted, the possibility of blood leakage through the seat of a loose O-ring is eliminated. The omission of the O-ring also contributes to cutting manufacturing costs. The possibility of the connecting ring 36 sustaining damage due to mechanical strain is eliminated because the interior thereof is kept filled with the adhesive agent. Even the formation of screw threads on parts comprising the junction of the two housings can be omitted. When these screw threads are omitted, the cost of production can be notably lowered and the alignment of the gas part and the water part is quite easily facilitated.

What is claimed is:

1. A heat exchanger-incorporated hollow fiber type artificial lung, comprising:
   a hollow fiber type artificial lung including:
     a first generally cylindrical housing having an inner wall,
     a hollow fiber bundle of a plurality of gas-exchange hollow fiber membranes mutually separated and parallelly disposed within said first housing in the axial direction of said first housing, said fiber membranes having respective openings,
     a first and a second partition at opposite ends of said first housing for water-tightly supporting said hollow fiber membranes at the opposite ends of said membranes without blocking the openings of the membranes and for defining an oxygen chamber in conjunction with the inner wall of said first housing and the outer surfaces of said hollow fiber membranes,
     an oxygen inlet and an oxygen outlet each for communicating with said oxygen chamber, and
     a first blood manifold for communicating blood to and from the interiors of said hollow fiber membranes at the openings thereof on the side of said first partition;
   a shell-and-tube type heat exchanger part including:
     a second generally cylindrical housing having an inner wall,
     a plurality of tubes mutually separated and parallelly disposed inside said second housing in the axial direction of said second housing, said tubes having respective openings,
     a third and a fourth partition at opposite ends of said second housing for water-tightly supporting said tubes at the opposite ends of said tubes without blocking the openings of said tubes and for defining a heat-exchange medium chamber in conjunction with the inner wall of said second housing and the outer surfaces of said tubes,
     a heat-exchange medium inlet and a heat-exchange medium outlet each for communicating with said heat-exchange medium chamber, and
     a second blood manifold for communicating blood to and from the interiors of said tubes at the openings thereof on the side of said fourth partition; and
   connecting means for joining said first and said second housings coaxially to one another so that said second partition at a connecting end of said first housing remote from said first blood manifold faces said third partition at a connecting end of said second housing remote from said second blood manifold, said connecting means forming at least a part of a blood chamber formed between said second partition and said third partition,
   said connecting means including:
     an annular spacer interposed between said third partitions, and abutting confronting faces of said second and said third partitions, said annular spacer having an inner wall defining a circumferential inner wall of said blood chamber formed between said second and third partitions, and said annular spacer having an outer periphery, said outer periphery having an annular protuberance thereon,
     a connecting ring arranged to be fitted across the outsides of said connecting ends of said first and said second housings, said connecting ring surrounding said annular spacer and being spaced outwardly of said outer periphery of said annular spacer, to form an annular space between said connecting ring and said annular spacer, said connecting ring having at least two injection holes therein to communicate with said annular space interior of said connecting ring, said annular space being defined by the inner periphery of said connecting ring, portions of confronting faces of said third and second partitions, and the outer periphery of said annular spacer, and
     an adhesive sealing agent injected through said injection holes of said connecting ring and filling up and sealing said annular space interior of said connecting ring and adhesively and liquid tightly fastening said first and second housings, said annular spacer, and said connecting ring to one another;
   whereby said artificial lung part and heat exchanger part are coaxially connected together so as to form a liquid tight blood chamber between said second partition and said third partition interior of said inner wall of said annular spacer 2. A heat exchanger-incorporated hollow fiber type artificial lung according to claim 1, wherein said first and second housings include corresponding connecting ends of an identical diameter.

3. A heat exchanger-incorporated hollow fiber type artificial lung according to claim 2, wherein said connecting ends of the first and second housings have screw threads cut thereon in mutually opposite spiralling directions and the first and second housings are connected to each other by said connecting ring fitted across the outsides of the connecting ends, said connecting ring having corresponding screw threads cut on the inner circumference thereof.

4. A heat exchanger-incorporated hollow fiber type artificial lung according to claim 1, wherein said protuberance is a continuous raised strip.

5. A heat exchanger-incorporated hollow fiber type artificial lung according to claim 1, wherein said raised strip is in a discontinuous form.

6. A heat exchanger-incorporated hollow fiber type artificial lung according to claim 1, wherein gaps are formed between said second and third partitions and said protuberance, and including an O-ring inserted in each gap.

7. A heat exchanger-incorporated hollow fiber type artificial lung according to claim 1, wherein said adhesive agent is a potting agent of relatively high polarity.

8. A heat exchanger-incorporated hollow fiber type artificial lung according to claim 7, wherein said potting agent is one member selected from the group consisting of polyurethane, silicone and epoxy resin.

9. A heat exchanger-incorporated hollow fiber type artificial lung according to claim 7, wherein said potting agent is polyurethane.

* * * * *